United States Patent [19]

Goddard

[11] 4,180,569
[45] Dec. 25, 1979

[54] SEED TREATMENT FUNGICIDES FOR CONTROL OF SEED-BORNE DISEASES

[75] Inventor: Steven J. Goddard, West Grove, Pa.

[73] Assignee: E. I. Du Pont de Nemours and Company, Wilmington, Del.

[21] Appl. No.: 920,079

[22] Filed: Jun. 28, 1978

Related U.S. Application Data

[63] Continuation-in-part of Ser. No. 757,227, Jan. 11, 1977, abandoned, which is a continuation-in-part of Ser. No. 705,151, Jul. 19, 1976, abandoned, which is a continuation-in-part of Ser. No. 660,034, Feb. 20, 1976, abandoned.

[51] Int. Cl.$^2$ .............................................. A01N 9/20
[52] U.S. Cl. .................................................. 424/226
[58] Field of Search ........................ 424/226; 260/156

[56] References Cited

U.S. PATENT DOCUMENTS

| | | | |
|---|---|---|---|
| 3,118,871 | 1/1964 | Brody et al. | 260/156 |
| 3,154,555 | 10/1964 | Dehlert | 260/294.8 |

FOREIGN PATENT DOCUMENTS

| | | | |
|---|---|---|---|
| 211712 | 7/1956 | Australia | 260/156 |
| 611935 | 1/1961 | Canada | 260/156 |

OTHER PUBLICATIONS

Chemical Abstracts 69: 42567b (1968) & Formula Index for vol. 66–75 (1967–1971).
Herlich et al.–Veterinary Medicine, May, 1961 pp. 219–221.

*Primary Examiner*—Leonard Schenkman

[57] ABSTRACT

This invention relates to a method for controlling seed-borne fungus diseases in plants, by applying to the seed a fungicidally effective amount of 4,4'-azodipyridine or acid salts of the formula

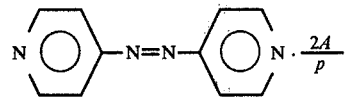

wherein
  A is an acid having acidic dissociation constant greater than $1 \times 10^{-6}$; and
  P is equal to the number of hydrogens on the acid A which have an acidic dissociation constant greater than $1 \times 10^{-6}$.

5 Claims, No Drawings

SEED TREATMENT FUNGICIDES FOR CONTROL OF SEED-BORNE DISEASES

CROSS REFERENCE TO RELATED APPLICATION

This application is a continuation-in-part of my copending application Ser. No. 757,227 filed Jan. 11, 1977, which is a continuation-in-part of Ser. No. 705,151, filed July 19, 1976, which is a continuation-in-part of my copending application Ser. No. 660,034, filed Feb. 20, 1976, all now abandoned.

BACKGROUND OF THE INVENTION

Fungi which infest seed are frequently capable of inflicting severe crop losses throughout the world. This is especially true of Helminthosporium species, such as H. oryzae, H. teres, H. sativum, H. gramineum and H. avenae, which attack most of the more important cereals and grasses including barley, wheat, rye, oats, sorghum, millet, rice, corn and cultivated grasses. Helminthosporium species produce various symptoms. For example, in rice, germination may be prevented or seedlings killed or distorted by dead leaf spots. In barley, lesions occur on the sheaths that cover the young shoots, and plants may be killed by root or basal rot. Immense numbers of spores may be produced on older plants which contaminate or infect developing seeds and serve to carry the fungus directly from one year's crop to the next.

In the past, compounds containing mercury have been applied to various seeds to disinfest them of fungi such as Helminthosporium. Recently, however, difficulties have been encountered with the use of mercury and it has been banned from the market, thus a replacement is needed.

SUMMARY OF THE INVENTION

According to this invention it has unexpectedly been found that fungi which infest seed may be controlled by applying to the seed an effective amount of 4,4'-azodipyridine or novel acid salts of formula I;

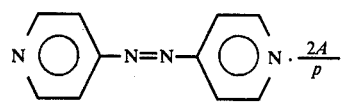

wherein
A is an acid having an acidic dissociation constant ($K_a$) greater than $1 \times 10^{-6}$; and
p is equal to the number of hydrogens on the acid A which have an acidic dissociation constant greater than $1 \times 10^{-6}$.

The acid salts of formula I are preferred for reasons of greater safety to formulators and applicators. Of the acid salts, 1,2-benzenedicarboxylate salt is preferred.

In particular, Helminthosporium species, such as H. oryzae, H. teres, H. sativum, H. gramineum and H. avenae, may be effectively controlled by the compounds and methods of this invention.

This invention also includes suitable agricultural compositions for controlling fungi on or in seed consisting essentially of a compound of this invention plus a surfactant or a liquid or a solid carrier. As used herein, the phrase "consisting essentially of" does not exclude the presence of other active pesticidal materials or conventional formulating ingredients.

DETAILED DESCRIPTION OF THE INVENTION

Synthesis of 4,4'-azodipyridine and Acid Salts

The process for preparing 4,4'-azodipyridine and the compound itself are disclosed in J. Chem. Soc., 5316 (1965).

The starting material, 4-aminopyridine is commercially available.

The azodipyridine is prepared by reaction of 4-aminopyridine with aqueous sodium hypochlorite.

The azodipyridinium salts are prepared by reacting 4,4'-azodipyridine in a suitable solvent at ambient temperature with an equivalent amount of an organic or inorganic acid having an acidic dissociation constant greater than $1 \times 10^{-6}$.

The following examples illustrate the method of preparation.

EXAMPLE 1

4,4'-Azodipyridine

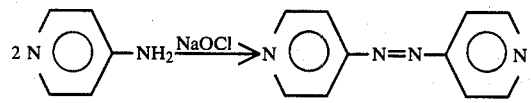

Sodium hypochlorite, 1000 ml (5.25%, 0.72 mole) was added dropwise to a cold solution (5° C.) of 50 g (0.5 mole) of 4-aminopyridine in 400 ml water. The sodium hypochlorite was added at such a rate as to maintain the reaction temperature at less than 10° C. After the addition was completed, the reactants were stirred for an additional 1½ hours at ~10° C. The resultant suspension was filtered and air dried to leave a crude brown solid. Recrystallization from methylcyclohexane yielded light orange crystals of 4,4'-azodipyridine, having a m.p. of 87°-89° C.

EXAMPLE 2

4,4'-Azodipyridinium-1,2-benzenedicarboxylate

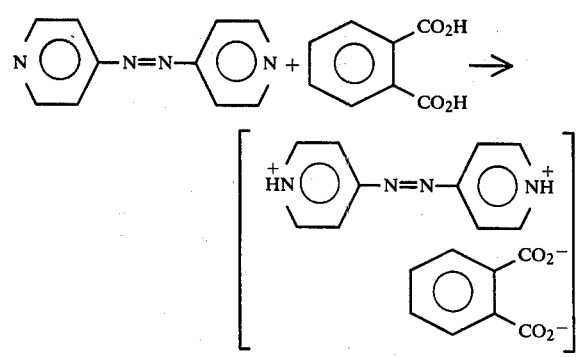

1,2-Benzenedicarboxylic acid, 1.66 g (0.01 mole) was added in one portion to a solution of 1.8 g (0.01 mole) of 4,4'-azodipyridine in 25 ml acetone. The reaction mixture was stirred at room temperature for one hour. The resultant suspension was filtered to leave an orange solid. Recrystallization from ethanol yielded 2.1 g of 4,4'-azodipyridinium-1,2-benzenedicarboxylate, having a m.p. of 171°-173° C.

The following 4,4'-azodipyridinium salts are prepared as in Example 2 by substituting the listed acid set forth in the table for the phthalic acid of Example 2.

| Acid Starting Reactant | M.P. of 4,4'-Azodipyridinium Salt |
| --- | --- |
| Adipic | 197°–200° C. |
| Butyric | 67°–67° C. |
| Oxalic | 208°–209° C. |
| Hydrochloric | >300° C. |
| 1,3-Benzenedicarboxylic | 247°–250° C. |
| Nitric | 195° C. |
| Sulfuric | 209°–212° C. |
| Stearic | 81°–83° C. |
| Benzoic | 138°–140° C. |
| Salicylic | 168°–170° C. |
| Lactic | 70°–78° C. |
| Citric | 149°–150° C. |
| Cinnamic | 133°–136° C. |
| Phenylacetic | 65°–68° C. |
| 1,4-Benzenedicarboxylic | >275° C. |
| Acetic | 94°–97° C. |
| Fumaric | 191°–192° C. |

Application

The compounds of this invention, 4,4'-azodipyridine and its acid salts, as indicated above, are capable of protecting seed from the adverse effect of various fungi and in particular Helminthosporium species. Among those seeds which can be protected by the application of the compounds of this invention are cereal grains such as barley, wheat, rye, oats, sorghum, millet, rice, corn, and cultivated grasses. Because of the activity of the compounds of this invention, they may be used at relatively low rates.

The compounds can be formulated and applied as a slurry, a solid seed coating, a soak, or as a dust on the surface of the seed. Needless to say, the method of application of the compounds to the seed may be varied and the invention is intended to include any technique which is to be used.

In general, the seed should be treated with about 5–1,000 grams of 4,4'-azodipyridine or its salts per 100 kilograms of seed, preferably about 10–500 grams per 100 kilograms of seed and most preferably about 20 to 250 grams per 100 kilograms of seed.

Formulations

Useful formulations of the compounds of this invention can be prepared in conventional ways. They include dusts, solutions, suspensions, emulsions, wettable powders, emulsifiable concentrates and the like. Many of these may be applied directly. Sprayable formulations can be used without dilution or can be extended in suitable media. High strength compositions are primarily used as intermediates for further formulation. The formulations, broadly, contain about 1% to 99% by weight of active ingredient and at least one of (a) about 0.1% to 20% surfactant(s) (b) about 2% to 99% solid or liquid diluent(s). More specifically, they will contain these ingredients in the following approximate proportions:

| | Percent by Weight | | |
| --- | --- | --- | --- |
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | |
| Dusts | 1–25 | 70–99 | 0–5 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

The compounds of this invention may be formulated or mixed in the seed treater tank or combined on the seed by overcoating with other seed treating agents. The agents to be mixed with the compounds of this invention may be for the control of pests, modification of growth, nutrition, or for the control of plant diseases. Agents for plant disease control include but are not limited to the following: benomyl (methyl N-[1-butylcarbamoyl)-2-benzimidazole]carbamate), carbendazim [methyl 2-benzimidazolecarbamate], Captan ® [N-(trichloromethylthio)3a, 4,7,7a-tetrahydrophthalimide], captafol [N-(1,1,2,2-tetrachloroethylthio)-3a,4,7,7a-tetrahydrophthalimide], maneb [manganese ethylene-1,2-bisdithiocarbamate], mancozeb, Vitavax ® [5,6-dihydro-2-methyl-1,4-oxathiin-3-carboxanilide], Ethirimol, Oxathiin, chloroneb [1,4-dichloro-2,5-dimethoxybenzene], thiram [bis(dimethylthiocarbamoyl)disulfide], Dexon ® [p-dimethylaminobenzenediazo sodium sulfonate]PCNB [pentachloronitrobenzene].

The compounds of this invention may also be formulated with insecticides to protect seed against destruction by insects during storage or after planting.

Typical solid diluents for use in formulating compounds of the instant invention are described in Watkins et al., "Handbook of Insecticide Dust Diluents and Carriers," 2nd. Edn., Dorland Books, Caldwell, N.J. The more absorptive diluents are preferred for wettable powders and the denser ones for dusts. Typical liquid diluents and solvents are described in Marsden, "Solvents Guide," 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual," MC Publ. Corp., Ridgewood, New Jersey, as well as Sisely and Wood, "Encyclopedia of Surface Active Agents," Chemical Publ. Co., Inc., New York, 1964, list surfactants and recommended uses. All formulations can also contain additives to reduce foam, caking, corrosion or microbiological growth, to reduce dustiness, to improve seed adherence, to color treated seed, to improve seed flow, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). See J. E. Browning, "Agglomeration," *Chemical Engineering,* Dec. 4, 1967, pp. 147ff. and "Perry's Chemical Engineer's Handbook," 4th Edn., McGraw-Hill, N. Y., 1963, pp. 8-59ff.

For further information regarding the art of formulation, see for example:

J. B. Buchanan, U.S. Pat. No. 3,576,834, Apr. 27, 1971, Col. 5, Line 36 through Col. 7, Line 70, and Exs. 1–4, 17, 106, 123–140.

R. R. Shaffer, U.S. Pat. No. 3,560,616, Feb. 2, 1971, Col. 3, Line 48 through Col. 7, Line 26 and Exs. 3–9, 11–18.

E. Somers, "Formulation," Chapter 6 in Torgeson, "Fungicides," Vol. I, Academic Press, New York, 1967.

This invention is further illustrated by the following examples:

EXAMPLE 3

Dust Seed Coat

| | |
|---|---|
| 4,4'-Azodipyridine | 75% |
| Permanent Red 2B, Calcium Salt, Extended on Blanc Fixe | 5% |
| Diatomaceous Earth | 20% |

The ingredients are blended, coarsely hammer-milled and passed through a fluid energy mill to produce particles of active ingredient that are all below 10 microns in diameter. The product is reblended before packaging.

EXAMPLE 4

Slurry Seed Coat

| | |
|---|---|
| 4,4'-Azodipyridine | 65% |
| Calcium Ligninsulfonate | 4% |
| Trimethylnonyl Polyethylene Glycol Ether | 4% |
| Rhodamine B | 1% |
| Permanent Red 2B, Calcium Salt, Extended on Blanc Fixe | 1% |
| Diatomaceous Earth | 25% |

The liquid surfactant is sprayed on the diatomaceous earth, the other ingredients are then added and thoroughly mixed together in an efficient blender. The mixture is then coarsely hammer-milled and passed through a fluid energy mill to produce particles of active ingredient that are less than 10 microns in diameter. The product is reblended before packaging.

EXAMPLE 5

Solution Seed Coat

| | |
|---|---|
| 4,4'-Azodipyridinium-1,2-benzenedicarboxylate | 20% |
| Dimethylformamide | 79.7% |
| Rhodamine B | 0.3% |

The materials are combined and stirred until a solution is obtained. The solution is applied directly to the seed.

EXAMPLE 6

Solution Seed Coat

| | |
|---|---|
| 4,4'-Azodipyridine | 20% |
| Dimethylformamide | 79.7% |
| Rhodamine B | 0.3% |

The materials are combined and stirred until a solution is obtained. The solution is applied directly to the seed.

EXAMPLE 7

A formulation wherein compounds of this invention are admixed with another seed treating agent is illustrated:

Solution Seed Coat

| | |
|---|---|
| 4,4'-Azodipyridine | 35% |
| Carbendazim | 35% |
| Permanent Red 2B, Calcium Salt, Extended on Blanc Fixe | 10% |
| Diatomaceous Earth | 20% |

The ingredients are blended and then processed in the same manner as Example 3, to produce a dust seed treatment.

The ability of the compounds of this invention to disinfect seed which is infested with a fungus, is illustrated by the following examples.

EXAMPLE 8

Barley and rice seed naturally infested with the fungi *Helminthosporium sativum* and *H. oryzae*, respectively, were added to 237 cc capacity glass bottles. Each bottle contained 10 grams of rice and 15 grams of barley seed. Samples were treated with the compound of this invention, 4,4'-azodipyridine, at different rates. The chemical was applied in an acetone:dimethylformamide (9:1) solution to the seed as it was tumbled. The treated seed was planted in sterile soil and placed on the greenhouse bench. Treated seed were grown for 14–18 days and observed for diseased tissue. Percent healthy was calculated by the formula:

$$\frac{\text{Number healthy in treatment}}{\text{Number seed planted per treatment}} \times 100$$

| | Active Ingredient (g.) per 100 kg | Percent Healthy | |
|---|---|---|---|
| Treatment | of seed | (Barley) | (Rice) |
| 4,4'-azodipyridine | 500 | 100 | 98 |
| | 250 | 92 | 96 |
| | 125 | 94 | 96 |
| | 63 | 96 | 90 |
| | 31 | 96 | 86 |
| | 16 | 82 | 70 |
| | untreated | 30 | 26 |
| | solvent treated | 38 | 24 |

EXAMPLE 9

Rice seed naturally infested with the fungus *Helminthosporium oryzae* was added to 20 cc capacity glass vials. Each vial contained 3 g of rice seed. Samples were treated with the compounds of this invention at different rates. The chemical was applied in an acetone-dimethylformamide (9:1) solution to the seed as it was tumbled. The treated seed was placed on an absorbent paper substrate which was moistened and placed in a moisture chamber for 14 days. The resulting rice plants were visually rated for percent control on a scale from 0–100, where 0 is 0% disease control and 100 is 100% disease control.

| 4,4'-Azodipyridine Acid Salt | Active Ingredient (g) per 100 kg of Seed | Percent Control (Rice) |
|---|---|---|
| Adipate | 250 | 80 |
|  | 125 | 80 |
|  | 63 | 80 |
| n-Butyrate | 250 | 80 |
|  | 125 | 80 |
|  | 63 | 80 |
| Oxalate | 250 | 50 |
|  | 125 | 50 |
|  | 63 | 30 |
| Chloride | 250 | 50 |
|  | 125 | 0 |
|  | 63 | 0 |
| 1,2-Benzenedicarboxylate | 250 | 90 |
|  | 125 | 90 |
|  | 63 | 90 |
| 1,3-Benzenedicarboxylate | 250 | 50 |
|  | 125 | 50 |
|  | 63 | 0 |
| Nitrate | 250 | 50 |
|  | 125 | 50 |
|  | 63 | 50 |
| Bisulfite | 250 | 50 |
|  | 125 | 50 |
|  | 63 | 0 |
| Fumarate | 250 | 70 |
|  | 125 | 80 |
|  | 63 | 100 |
| Benzoate | 250 | 70 |
|  | 125 | 70 |
|  | 63 | 60 |
| Salicylate | 250 | 60 |
|  | 125 | 50 |
|  | 63 | 50 |
| Lactate | 250 | 50 |
|  | 125 | 60 |
|  | 63 | 50 |
| Citrate | 250 | 50 |
|  | 125 | 50 |
|  | 63 | 40 |
| Cinnamate | 250 | 60 |
|  | 125 | 60 |
|  | 63 | 50 |
| Phenylacetate | 250 | 70 |
|  | 125 | 50 |
|  | 63 | 30 |
| 1,4-Benzenedicarboxylate | 250 | 60 |
|  | 125 | 60 |
|  | 63 | 30 |
| Acetate | 250 | 60 |
|  | 125 | 60 |
|  | 63 | 30 |

EXAMPLE 10

EYE IRRITATION TEST IN RABBITS

Procedure:

10 Mgs. of undiluted solid 4,4'-azodipyridine and 4,4'-azodipyridinium-1,2-benzenedicarboxylate were placed into the right conjunctival sac of two albino rabbits. After 20 seconds, one treated eye was washed with tap water for one minute. The treated eye of the other rabbit was not washed. Observations of the cornea, iris and conjunctiva were made with a hand-slit lamp at one and four hours, and at one, two, three, eight and fourteen days; Fluor-i-strip ® stain and a biomicroscope were used at examinations after the day of treatment.

Summary:

4,4'-Azodipyridine produced mild corneal opacity with moderate to severe corneal swelling, moderate iritis with flare and severe conjunctival irritation in an unwashed rabbit eye. An eye treated and promptly washed had slight corneal opacity with mild corneal swelling, transient mild iritis and moderate conjunctival irritation. The washed eye was normal in 8 days while the unwashed eye had receding corneal opacity with attendant vascularization remaining at 14 days.

4,4'-Azodipyridine is a moderate to severe eye irritant which is capable of causing permanent corneal opacity. Washing lessened the duration and severity of ocular effects. However, eye contact with this compound should be strictly avoided. In the event of an eye exposure, immediate copious flushing with water should be followed by prompt expert medical attention.

4,4'-Azodipyridinium-1,2-benzenedicarboxylate produced a moderate area of slight corneal opacity and mild conjunctivitis with no iritic effect in a rabbit eye. The opacity was reversible and the eye was normal within 3 days except for a persistent mild conjunctival irritation which was normal within 7 days. An eye dosed with the compound and promptly washed had slight conjunctivitis which no corneal or iritic effect and was normal within 3 days.

Although only temporary mild ocular effects occurred, good hygienic practice would be to flush copiously with water after any eye contact with this material.

I claim:

1. A method for controlling fungi which infest seeds comprising applying to the seeds a fungicidally effective amount of a compound selected from the group consisting of 4,4'-azodipyridine and 4,4'-azodipyridinium acid salts of the formula

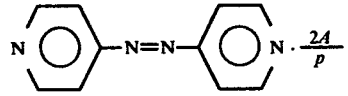

wherein

A is an acid having an acidic dissociation constant greater than $1 \times 10^{-6}$; and p is equal to the number of hydrogens on the acid A which have an acidic dissociation constant greater than $1 \times 10^{-6}$.

2. The method of claim 1 wherein the compound is 4,4'-azodipyridine.

3. The method of claim 1 wherein the compound is a 4,4'-azodipyridinium acid salt.

4. The method of claim 3 wherein the acid salt is 4,4'-azodipyridinium-1,2-benzenedicarboxylate.

5. The method of claim 1 wherein 10–500 grams of the compound is applied per kilogram of cereal seed for control of Helminthosporium.

* * * * *